United States Patent [19]
François et al.

[11] Patent Number: 5,744,484
[45] Date of Patent: Apr. 28, 1998

[54] LUBELUZOLE INTRAVENOUS SOLUTIONS

[75] Inventors: Marc Karel Jozef François, Kalmthout; Jozef Peeters, Beerse; Christiane Grabriëlla Gerardus Maria Heyns, Vosselaar, all of Belgium

[73] Assignee: Janssen Pharmaceutica, N.V., Beerse, Belgium

[21] Appl. No.: 817,740

[22] PCT Filed: Nov. 16, 1995

[86] PCT No.: PCT/EP95/04520

§ 371 Date: Apr. 23, 1997

§ 102(e) Date: Apr. 23, 1997

[87] PCT Pub. No.: WO96/15790

PCT Pub. Date: May 30, 1996

[30] Foreign Application Priority Data

Nov. 24, 1994 [EP] European Pat. Off. ............ 94203422

[51] Int. Cl.$^6$ .................................................. A61K 31/445
[52] U.S. Cl. .................................................. 514/321
[58] Field of Search ............................................. 514/321

[56] References Cited

U.S. PATENT DOCUMENTS 5,010,198  4/1991  Stokbroekx et al. ............... 546/114
5,434,168  7/1995  Stokbroekx et al. ............... 514/321

Primary Examiner—Phyllis G. Spivack
Attorney, Agent, or Firm—Ellen Ciambrone Coletti

[57] ABSTRACT

A solution is disclosed for intravenous administration containing lubeluzole or a pharmaceutically acceptable addition salt thereof, an isotonizing agent, water and acid and base substances to adjust the pH of the solution in the range from 2.5 to 3.6.

15 Claims, No Drawings

LUBELUZOLE INTRAVENOUS SOLUTIONS

CROSS-REFERENCE TO RELATED APPLICATIONS

This application is the national stage of application No. PCT/EP 95/04520, filed on Nov. 16, 1995, which application claims priority from EP 94.203.422.4, filed on Nov. 24, 1994.

In U.S. Pat. No. 4,861,785 there are described benzoxazol- and benzothiazolamine derivatives having anti-anoxic activity. In WO-92/14,731 some of these benzothiazolamine derivatives were disclosed having useful anti-stroke activity. The subject invention furnishes injectable formulations of (S)-4[(2-benzothiazolyl) methylamino]-α-[(3,4-difluorophenoxy)methyl]-1-piperidineethanol (generically known as lubeluzole) having excellent physical stability.

The most appropriate route of administration for the treatment of patients suffering from acute stroke probably is the direct infusion of the drug in the veins. A pharmaceutical formulation for intravenous administration has to comply with strict requirements regarding physical, chemical and biological stability. For example, problems may arise due to adsorption of the active ingredient to the walls of the i.v. administration equipment. In particular, substances tend to adsorb to the walls of the infusion bag and the PVC tubes in such equipment.

WO-92/14,731 discloses an injectable solution having pH 4 and containing a benzothiazolylamine derivative, glucose, hydrochloric acid, sodium hydroxide, hydroxypropyl-β-cyclodextrin and water. The latter solution comprising lubeluzole shows significant problems regarding adsorption to the walls of the i.v. equipment. It was found that the adsorption of lubeluzole to the walls of the i.v. administration equipment could be significantly reduced by maintaining the pH of the formulation below 3.6. In this way, an intravenous solution was prepared having superior physical stability when compared to the art formulation.

Hence, the present invention is concerned with a solution for intravenous administration containing water, lubeluzole or a pharmaceutically acceptable addition salt thereof, an isotonizing agent, and acid and base substances to adjust the pH of the solution in the range from 2.5 to 3.6.

The present invention also relates to the use of acid and base substances in a solution according to the invention for preventing adsorption of lubeluzole or a pharmaceutically acceptable addition salt thereof to the walls of the i.v. administration equipment.

Lubeluzole is generic to (S)-4-[(2-benzothiazolyl) methylamino]-α-[(3,4-difluoro-phenoxy)methyl]-1-piperidineethanol. Its preparation and properties are described in WO-92/14,731.

The addition salts as mentioned hereinabove are meant to comprise the therapeutically active non-toxic addition salt forms which lubeluzole is able to form. The latter can conveniently be obtained by treating the base form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids. Conversely the salt form can be converted into the free base form by treatment with alkali.

The term addition salt as used hereinabove also comprises the solvates which lubeluzole is able to form and said solvates are meant to be included within the scope of the present invention. Examples of such solvates are, e.g. the hydrates, alcoholates and the like.

The term "physically stable" as used herein refers to a solution for which less than 10% by weight of active ingredient is adsorbed after passing through an infusion device. Preferably less than 5% by weight of active ingredient is adsorbed.

Hereinafter, the amounts of each of the ingredients in the compositions are expressed as percentages by weight based on the total volume of the formulation, unless otherwise indicated.

In one particular aspect of the invention, the concentration of lubeluzole or a pharmaceutically acceptable addition salt thereof in the present solutions may range from 0.005% to 5%, preferably from 0.01% to 1%, more preferably from 0.02% to 0.2% and in particular is about 0.05%.

Further, the solutions in this aspect of the invention conveniently comprise from 1 to 10% isotonizing agent, in particular glucose is used as isotonizing agent. The use of glucose as isotonizing agent has the advantage that very clear solutions are obtained. Preferably, glucose is used in a concentration from 2 to 10%, most preferably of about 5%.

In another particular aspect of the present invention, the concentration of lubeluzole or a pharmaceutically acceptable addition salt thereof in the solutions may range from 0.005% to 5%, preferably from 0.005% to 0.1%, more preferably from 0.01% to 0.05% and in particular is about 0.02%.

Further, the solutions in this aspect of the invention conveniently comprise from 0.1 to 2% isotonizing agent, in particular sodium chloride is used as isotonizing agent. The use of sodium chloride as isotonizing agent is particularly useful for solutions wherein the concentration of lubeluzole ranges from 0.005% to 0.1%, preferably between 0.005% to 0.05%. Preferably, sodium chloride is used in a concentration from 0.4% to 1.8%, most preferably of about 0.9%.

The subject solutions further comprise acid and base substances to maintain the pH of the solution in the range from 2.5 to 3.6, preferably in the range from 3.0 to 3.4, most preferably at about 3.2. Preferably, the pH of the solutions is adjusted by appropriate amounts of hydrochloric acid and sodium hydroxide. The pH may also be adjusted by buffer systems comprising mixtures of appropriate amounts of an acid such as phosphoric, tartaric or citric acid, and a base, in particular sodium hydroxide.

In order to increase the solubility of lubeluzole or a pharmaceutically acceptable addition salt thereof in the present formulations, a solubilizer may be used. Conveniently, a cyclodextrin (CD) or a derivative thereof may be used.

Appropriate cyclodextrin derivatives are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl; hydroxy$C_{1-6}$alkyl, particularly hydroxyethyl, hydroxypropyl or hydroxy-butyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyl-oxy$C_{1-6}$alkyl, particularly carboxymethoxypropyl or carboxyethoxypropyl; $C_{1-6}$alkylcarbonyloxy-$C_{1-6}$alkyl, particularly 2-acetyloxypropyl. Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD.

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S.value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin hydroxyalkyl derivatives for use in the compositions according to the present invention the M.S. as determined by mass spectrometry is in the range of 0.125 to 10, in particular of 0.3 to 3, or from 0.3 to 1.5. Preferably the M.S. ranges from about 0.3 to about 0.8, in particular from about 0.35 to about 0.5 and most particularly is about 0.4. M.S. values determined by NMR or IR preferably range from 0.3 to 1, in particular from 0.55 to 0.75.

The average substitution degree (D.S.) refers to the average number of substituted hydroxyls per anhydroglucose unit. The D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. In the cyclodextrin derivatives for use in the compositions according to the present invention the D.S. as determined by MS is in the range of 0.125 to 3, in particular of 0.2 to 2 or from 0.2 to 1.5. Preferably the D.S. ranges from about 0.2 to about 0.7, in particular from about 0.35 to about 0.5 and most particularly is about 0.4. D.S. values determined by NMR or IR preferably range from 0.3 to 1, in particular from 0.55 to 0.75. More particular β- and γ-cyclodextrin hydroxyalkyl derivatives for use in the compositions according to the present invention are partially substituted cyclodextrin derivatives wherein the average degree of alkylation at hydroxyl groups of different positions of the anhydroglucose units is about 0% to 20% for the 3 position, 2% to 70% for the 2 position and about 5% to 90% for the 6 position. Preferably the amount of unsubstituted β- or γ-cyclodextrin is less than 5% of the total cyclodextrin content and in particular is less than 1.5%. Another particularly interesting cyclodextrin derivative is randomly methylated β-cyclodextrin.

Most preferred cyclodextrin derivatives for use in the present invention are those partially substituted β-cyclodextrin ethers or mixed ethers having hydroxypropyl, hydroxyethyl and in particular 2-hydroxypropyl and/or 2-(1-hydroxypropyl) substituents. The most preferred cyclodextrin derivative for use in the compositions of the present invention is hydroxypropyl-β-cyclodextrin having a M.S. in the range of from 0.35 to 0.50 and containing less than 1.5% unsubstituted β-cyclodextrin. M.S. values determined by NMR or IR preferably range from 0.55 to 0.75.

In order to minimize the risk of adverse reactions, an intravenous formulation preferably contains as few ingredients as possible. Therefore, a formulation without a solubilizer (e.g. a cyclodextrin) is preferred. It was found that, for formulations without a solubilizer, the solubility of lubeluzole in the present formulations ranges between about 9.2 mg/ml (pH 2.5) and about 2 mg/l (pH 3.6). Formulations of pH 3.2 without a solubilizer comprise at maximum about 3 mg/ml dissolved lubeluzole. Further, the subject solutions preferably do not contain a preservative. In order to ensure biological stability, the solutions are conveniently manufactured in unit-dose containers, e.g. unit-dose sachets or bottles, ampoules, and the like. It may also be advantageous to manufacture the solutions of the present invention in pre-filled syringes, in particular pre-filled syringes adapted for use with infusor devices.

The present solutions are conveniently used in the treatment of patients suffering from acute stroke. In general it is contemplated that an effective daily amount would be from 0.1 to 100 mg, preferably from 1 to 50 mg of active ingredient. It is evident that said effective daily amount may be lowered or increased depending on the response of the treated subject and/or depending on the evaluation of the physician prescribing the compounds of the instant invention. The effective daily amount ranges mentioned hereinabove are therefore guidelines only and are not intended to limit the scope or use of the invention to any extent. The subject solutions may conveniently be co-administered with a physiologic salt solution according to art-known infusion procedures.

One aspect of the invention particularly relates to solutions comprising:
   (a) 0.005 to 5% lubeluzole or a pharmaceutically acceptable addition salt thereof;
   (b) 1 to 10% isotonizing agent;
   (c) acid and/or base substances to adjust the pH in the range from 2.5 to 3.6; and
   (d) water q.s. ad 100%.

Preferably, this aspect of the invention relates to solutions comprising:
   (a) 0.01 to 1% lubeluzole or a pharmaceutically acceptable addition salt thereof;
   (b) 2 to 10% glucose;
   (c) hydrochloric acid and sodium hydroxide to adjust the pH in the range from 3.0 to 3.4; and
   (d) water q.s. ad 100%.

Another aspect of the present invention particularly relates to solutions comprising:
   (a) 0.005 to 5% lubeluzole or a pharmaceutically acceptable addition salt thereof;
   (b) 0.1 to 2% isotonizing agent;
   (c) acid and/or base substances to adjust the pH in the range from 2.5 to 3.6; and
   (d) water q.s. ad 100%.

Preferably, this aspect of the invention relates to solutions comprising:
   (a) 0.005 to 0.1% lubeluzole or a pharmaceutically acceptable addition salt thereof;
   (b) 0.4 to 1.8% sodium chloride;
   (c) hydrochloric acid and sodium hydroxide to adjust the pH in the range from 3.0 to 3.4; and
   (d) water q.s. ad 100%.

Optionally, the above formulations further comprise a cyclodextrin or a derivative thereof.

Most preferably, the invention in all its aspects relates to solutions containing approximately:
   (a) 0.05% lubeluzole or a pharmaceutically acceptable addition salt thereof;
   (b) 5% glucose;

(c) hydrochloric acid and sodium hydroxide to adjust the pH to about 3.2; and (d) water q.s. ad 100%;

and to solutions containing approximately:

(a) 0.02% lubeluzole or a pharmaceutically acceptable addition salt thereof;

(b) 0.9% sodium chloride;

(c) hydrochloric acid and sodium hydroxide to adjust the pH to about 3.2; and (d) water q.s. ad 100%;

Further, the present invention relates to the preparation of the described solutions. The preparation involves the intimate mixing of the active ingredient with water, the isotonizing agent and the acid and base substances. In particular, the preparation involves the following steps:

(a) the active ingredient, the isotonizing agent and the acid are mixed with an appropriate amount of water;

(b) the base is added in an amount sufficient to reach the desired pH; and (c) water is added to the desired end volume.

Optionally, the solution is sterilized using art-known techniques.

The above procedure may be conducted under an inert atmosphere, e.g. nitrogen or oxygen-free argon. It is advantageous to use a micronized form of lubeluzole or a pharmaceutically acceptable addition salt thereof, in particular material having an average particle size of less than 100 microns, preferably less than 75 microns, and in particular having a mean particle size of not more than 15 microns. Micronized forms can be prepared by micronization techniques known in the art, e.g. by milling in appropriate mills and sieving through appropriate sieves.

Since the product is meant to be administered acutely to patients suffering form stroke, that is in the ambulance, emergency room or intensive care unit, an infusion pack for the acute treatment of stroke comprising the product together with a disposable, independent drive unit is considered to be the most useful presentation of the product according to the present invention. As independent drive units for powering syringes, in particular pre-filled syringes, there may be named both gas-operated and vacuum-operated drive units, the latter being preferred for their more reliable flow control.

The following examples are intended to illustrate the scope of the present invention in all its aspects.

EXAMPLE 1

F1

| Ingredient | Quantity |
| --- | --- |
| Lubeluzole | 0.5 mg |
| Glucose anhydrous | 50 mg |
| Concentrated hydrochloric acid | 0.332 μl |
| Sodium hydroxide | q.s. ad pH = 3.2 |
| Water for injections | q.s. ad 1 ml |

Preparation:

(a) 0.5 mg lubeluzole, 50 mg glucose anhydrous and 0.332 μl concentrated hydrochloric acid were mixed with 0.8 ml water;

(b) sodium hydroxide was added until pH=3.2±0.1; and (c) water was added to 1 ml.

In a similar way there were prepared:

| Ingredient | Quantity |
| --- | --- |
| F2 | |
| Lubeluzole | 1 mg |
| Glucose anhydrous | 50 mg |
| Concentrated hydrochloric acid | 0.489 μl |
| Sodium hydroxide | q.s. ad pH = 3.2 |
| Water for injections | q.s. ad 1 ml |
| F3 | |
| Lubeluzole | 0.5 mg |
| Glucose anhydrous | 50 mg |
| Concentrated hydrochloric acid | 0.332 μl |
| Sodium hydroxide | q.s. ad pH = 3.1 |
| Water for injections | q.s. ad 1 ml |
| F4 | |
| Lubeluzole | 0.2 mg |
| Sodium chloride | 9 mg |
| Concentrated hydrochloric acid | 0.192 μl |
| Sodium hydroxide | q.s. ad pH = 3.2 |
| Water for injections | q.s.ad 1 ml |
| F5 | |
| Lubeluzole | 0.25 mg |
| Glucose anhydrous | 50 mg |
| Concentrated hydrochloric acid | 0.25 μl |
| Sodium hydroxide | q.s. ad pH = 3.2 |
| Water for injections | q.s. ad 1 ml |

EXAMPLE 2

PHYSICAL STABILITY

The above solutions were pumped through an infusion device at a rate of 10 ml/hour for 48 hours. Fractions were collected at different time intervals and the concentration of lubeluzole was determined. The adsorbed percentage (by weight) of lubeluzole was less than 4% at any moment during the experiment. Hence, the described solutions are in compliance with the requirements of a physically stable formulation as set forth hereinabove.

We claim:

1. A solution for intravenous administration containing water, lubeluzole or a pharmaceutically acceptable addition salt thereof, an isotonizing agent, and acid and base substances to adjust the pH of the solution in the range from 2.5 to 3.6.

2. A solution according to claim 1 wherein the isotonizing agent is glucose.

3. A solution according to claim 1 comprising acid and base substances to adjust the pH of the solution in the range from 3.0 to 3.4.

4. A solution according to claim 1 comprising:

(a) 0.005 to 5% lubeluzole or a pharmaceutically acceptable addition salt thereof;

(b) 1 to 10% isotonizing agent;

(c) acid and/or base substances to adjust the pH in the range from 2.5 to 3.6; and (d) water q.s. ad 100%.

5. A solution according to claim 4 comprising:

(a) 0.01 to 1% lubeluzole or a pharmaceutically acceptable addition salt thereof;

(b) 2 to 10% glucose;

(c) hydrochloric acid and sodium hydroxide to adjust the pH in the range from 3.0 to 3.4; and (d) water q.s. ad 100%.

6. A solution according to claim 5 containing approximately:

(a) 0.05% lubeluzole or a pharmaceutically acceptable addition salt thereof;

(b) 5% glucose;

(c) hydrochloric acid and sodium hydroxide to adjust the pH to about 3.2; and (d) water q.s. ad 100%.

7. A solution according to claim 1 wherein the isotonizing agent is sodium chloride.

8. A solution according to claim 1 comprising:

(a) 0.005 to 5% lubeluzole or a pharmaceutically acceptable addition salt thereof;

(b) 0.1 to 2% isotonizing agent;

(c) acid and/or base substances to adjust the pH in the range from 2.5 to 3.6; and (d) water q.s. ad 100%.

9. A solution according to claim 8 comprising:

(a) 0.005 to 0.1% lubeluzole or a pharmaceutically acceptable addition salt thereof;

(b) 0.4 to 1.8% sodium chloride;

(c) hydrochloric acid and sodium hydroxide to adjust the pH in the range from 3.0 to 3.4; and (d) water q.s. ad 100%.

10. A solution according to claim 9 containing approximately:

(a) 0.02% lubeluzole or a pharmaceutically acceptable addition salt thereof;

(b) 0.9% sodium chloride;

(c) hydrochloric acid and sodium hydroxide to adjust the pH to about 3.2; and (d) water q.s. ad 100%.

11. A pre-filled syringe comprising a solution according to any one of claims 1 to 10.

12. A pre-filled syringe according to claim 11 adapted for use with infusor devices.

13. An infusion pack for the acute treatment of stroke comprising a solution according to any one of claims 1 to 10, and a disposable, independent drive unit.

14. An infusion pack according to claim 13 wherein the independent drive unit is gas-operated or vaccuum-operated.

15. An infusion pack for the acute treatment of stroke comprising a solution according to any of claims 1 to 10, and a disposable, independent drive unit, wherein the solution is contained in a pre-filled syringe adapted for use with infusor devices.

* * * * *